United States Patent
Sridharan (10) Patent No.: US 7,195,638 B1
(45) Date of Patent: Mar. 27, 2007

(54) CATHETER BALLOON

(75) Inventor: Srinivasan Sridharan, Morgan Hill, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 501 days.

(21) Appl. No.: 10/331,858

(22) Filed: Dec. 30, 2002

(51) Int. Cl.
*A61M 29/00* (2006.01)

(52) U.S. Cl. .................................................. 606/194

(58) Field of Classification Search ............. 604/96.01, 604/103.06, 103.08, 103.09; 606/192–194
See application file for complete search history.

(56) References Cited

U.S. PATENT DOCUMENTS

| | | | |
|---|---|---|---|
| 5,374,473 A | 12/1994 | Knox et al. | |
| 5,766,201 A * | 6/1998 | Ravenscroft et al. | 606/194 |
| 5,788,626 A | 8/1998 | Thompson | |
| 5,868,704 A | 2/1999 | Campbell et al. | |
| 6,016,848 A | 1/2000 | Egres, Jr. | |
| 6,048,356 A | 4/2000 | Ravenscroft et al. | |
| 6,120,477 A | 9/2000 | Campbell et al. | |
| 6,152,944 A * | 11/2000 | Holman et al. | 623/1.11 |
| 6,344,045 B1 * | 2/2002 | Lim et al. | 606/108 |
| 6,428,506 B1 * | 8/2002 | Simhambhatla et al. | 604/96.01 |
| 6,929,768 B2 * | 8/2005 | Sridharan et al. | 264/400 |
| 2003/0074016 A1 * | 4/2003 | Campbell et al. | 606/192 |

FOREIGN PATENT DOCUMENTS

| | | |
|---|---|---|
| WO | WO 95/05555 | 2/1995 |
| WO | WO 97/02791 | 1/1997 |

OTHER PUBLICATIONS

US 6,413,270, 07/2002, Thornton et al. (withdrawn)

* cited by examiner

*Primary Examiner*—Anhtuan T. Nguyen
*Assistant Examiner*—Elizabeth Houston
(74) *Attorney, Agent, or Firm*—Fulwider Patton LLP (57) ABSTRACT

An expandable medical device or component thereof including a tubular body formed of a wrapped sheet of porous polymeric material fused together, the tubular body having a fused seam at an angle relative to the longitudinal axis of the tubular body which changes along the length of the tubular body from a first angle to a second angle greater than the first angle. The sheet of porous polymeric material is wound and then fused together such that the winding angle is less in a first longitudinal section of the tubular body compared with the winding angle in a second longitudinal section of the tubular body, in order to provide the second section with greater resistance to expansion (i.e., lower compliance) than the first section.

11 Claims, 3 Drawing Sheets

CATHETER BALLOON

BACKGROUND OF THE INVENTION

This invention generally relates to medical devices, and particularly to intracorporeal devices for therapeutic or diagnostic uses such as balloon catheters, and vascular grafts.

In percutaneous transluminal coronary angioplasty (PTCA) procedures, a guiding catheter is advanced until the distal tip of the guiding catheter is seated in the ostium of a desired coronary artery. A guidewire, positioned within an inner lumen of a dilatation catheter, is first advanced out of the distal end of the guiding catheter into the patient's coronary artery until the distal end of the guidewire crosses a lesion to be dilated. Then the dilatation catheter having an inflatable balloon on the distal portion thereof is advanced into the patient's coronary anatomy, over the previously introduced guidewire, until the balloon of the dilatation catheter is properly positioned across the lesion. Once properly positioned, the dilatation balloon is inflated with fluid one or more times to a predetermined size at relatively high pressures (e.g. greater than 8 atmospheres) so that the stenosis is compressed against the arterial wall and the wall expanded to open up the passageway. Generally, the inflated diameter of the balloon is approximately the same diameter as the native diameter of the body lumen being dilated so as to complete the dilatation but not overexpand the artery wall. Substantial, uncontrolled expansion of the balloon against the vessel wall can cause trauma to the vessel wall. After the balloon is finally deflated, blood flow resumes through the dilated artery and the dilatation catheter can be removed therefrom.

In such angioplasty procedures, there may be restenosis of the artery, i.e. reformation of the arterial blockage, which necessitates either another angioplasty procedure, or some other method of repairing or strengthening the dilated area. To reduce the restenosis rate and to strengthen the dilated area, physicians frequently implant a stent inside the artery at the site of the lesion. Stents may also be used to repair vessels having an intimal flap or dissection or to generally strengthen a weakened section of a vessel. Stents are usually delivered to a desired location within a coronary artery in a contracted condition on a balloon of a catheter which is similar in many respects to a balloon angioplasty catheter, and expanded to a larger diameter by expansion of the balloon. The balloon is deflated to remove the catheter and the stent left in place within the artery at the site of the dilated lesion. Stent covers on an inner or an outer surface of the stent have been used in, for example, the treatment of pseudo-aneurysms and perforated arteries, and to prevent prolapse of plaque. Similarly, vascular grafts comprising cylindrical tubes made from tissue or synthetic materials such as polyester, expanded polytetrafluoroethylene, and DACRON may be implanted in vessels to strengthen or repair the vessel, or used in an anastomosis procedure to connect vessels segments together.

In the design of catheter balloons, characteristics such as strength, compliance, and profile of the balloon are carefully tailored depending on the desired use of the balloon catheter, and the balloon material and manufacturing procedure are chosen to provide the desired balloon characteristics. A variety of polymeric materials are conventionally used in catheter balloons. Use of polymeric materials such as PET that do not stretch appreciably consequently necessitates that the balloon is formed by blow molding, and the deflated balloon material is folded around the catheter shaft in the form of wings, prior to inflation in the patient's body lumen. However, it can be desirable to employ balloons, referred to as formed-in-place balloons, that are not folded prior to inflation, but which are instead expanded to the working diameter within the patient's body lumen from a generally cylindrical or tubular shape (i.e., essentially no wings) that conforms to the catheter shaft.

Catheter balloons formed of expanded polytetrafluoroethylene (ePTFE), which are inflated within the patient's body lumen without blow molding the ePTFE tubing, have been disclosed. Prior methods of forming the ePTFE balloon involved wrapping a sheet of ePTFE on a mandrel and then heating the wrapped sheet to fuse the layers of wrapped material together. One difficulty has been the failure of the bond between the ePTFE balloon and the catheter shaft at relatively low inflation pressures.

It would be a significant advance to provide a catheter balloon with improved performance characteristics and ease of manufacture.

SUMMARY OF THE INVENTION

This invention is directed to an expandable medical device or component thereof with a tubular body formed of a wrapped sheet of porous polymeric material fused together, the tubular body having a fused seam at an angle relative to the longitudinal axis of the tubular body, and the angle of the fused seam changes along the length of the tubular body from a first angle to a second angle greater than the first angle. The sheet of porous polymeric material is wound and then fused together such that the winding angle in a first longitudinal section of the tubular body is less than the winding angle in a second longitudinal section of the tubular body, in order to provide the second section with greater resistance to expansion (i.e., lower compliance) than the first section.

In a presently preferred embodiment, the tubular body has a centrally located section with the fused seam at the first angle. In one embodiment, the tubular body has a distal section with the fused seam at the second angle greater than the first angle (i.e., the second angle is more nearly perpendicular relative to the longitudinal axis of the tubular body than is the first angle). Typically, a proximal section of the tubular body has the fused seam at a third angle greater than the first angle. The second and third angles are preferably about equal, although in alternative embodiments the third angle can be less than or greater than the second angle. In one embodiment, the angle of the fused seam changes from the first angle to an intermediate angle between the first and second angles, to provide multiple changes in the resistance to expansion along the length of the tubular body. Similarly, in one embodiment, the angle of the fused seam changes from the first angle to an intermediate angle between the first and third angles.

In a presently preferred embodiment, the expandable medical device is an inflatable balloon for a catheter. The balloon can be used on a variety of suitable balloon catheters including coronary and peripheral dilatation catheters, stent delivery catheters, drug delivery catheters and the like. Although discussed below primarily in terms of the embodiment in which the medical device is an inflatable member such as a balloon for a catheter, it should be understood that other expandable medical devices are included within the scope of the invention, including stent covers and vascular grafts. The catheter balloon typically has a proximal skirt section and a distal skirt section bonded to the catheter shaft so that the interior of the balloon is in fluid communication with an inflation lumen in the shaft. The balloon has an inflatable working section between the skirt sections which expands during inflation of the balloon to perform a procedure such as dilating a stenosis or implanting a stent, and has inflated sections on either end of the inflated central working section tapering towards the skirt sections.

In a presently preferred embodiment, the fused seam at the first angle extends along at least a portion of the balloon working section, and the fused seam at the second angle extends along at least a portion of one of the proximal or distal skirt sections. For example, in one embodiment, at least a portion of the distal skirt section has the fused seam at the second angle greater than the first angle, and at least a portion of the proximal skirt section has the fused seam at the third angle greater than the first angle. Thus, the skirt sections, with the fused seam of the porous polymeric material at the second angle greater than the first angle relative to the longitudinal axis of the balloon, have a greater resistance to expansion than the working length during inflation of the balloon. As a result, the burst pressure of the balloon is increased because the bond strength of the skirt sections is increased. The higher wrap angle of the skirt sections is believed to provide increased resistance to radial expansion by inhibiting the tendency of the angle of fused seam to increase due to rotation of the wrapped porous polymeric sheet during inflation of the balloon. In one embodiment, the balloon has a burst pressure (bond seal strength) of about 200 to about 350 psi, preferably about 250 to about 350 psi. In addition to an improved, increased burst pressure, the increased bond strength in a preferred embodiment provides increased fatigue resistance so that the balloon can be inflated multiple times without the bond between the balloon and shaft failing.

The proximal and distal inflatable sections (commonly referred to as the tapered or cone sections of the inflated balloon), located between the skirt sections and the central working section, may have the fused seam at the first angle, the second and third angles, or an intermediate angle between the first angle and the second and third angles along all or a portion of the lengths thereof. For example, in one embodiment, a first portion of the inflatable distal section has the fused seam with the second angle, and a second portion of the inflatable distal section has the fused seam with an intermediate angle between the first angle and the second angle. Consequently, the proximal and distal inflatable sections which are located at either end of the working length and which inflate to a tapered configuration are provided with more resistance to expansion than the working length, and expand to a smaller diameter than the working length, to further increase to burst pressure of the balloon.

In a presently preferred embodiment, the wrapped sheet of porous polymeric material comprises a polymer selected from the group consisting of expanded polytetrafluoroethylene (ePTFE), an ultra high molecular weight polyolefin such as ultra high molecular weight polyethylene, porous polyethylene, porous polypropylene, porous polyurethane, and porous nylon. In one embodiment, the porous material has a node and fibril microstructure. For example, ePTFE and ultra high molecular weight polyethylene (also referred to as "expanded ultra high molecular weight polyethylene") typically have a node and fibril microstructure, and are not melt extrudable. The node and fibril microstructure, when present, is produced in the material using conventional methods. In the embodiment in which the polymeric material of the balloon has a node and fibril microstructure, after the fused seam is formed, the tubular body of porous polymeric material is typically further processed, as for example by being stretched, heated, compacted, and heated a final time, to form the balloon. However, a variety of suitable polymeric materials can be used in the method of the invention, including conventional catheter balloon materials which are melt extrudable. In one presently preferred embodiment, the polymeric material cannot be formed into a balloon by conventional balloon blow molding, and is formed into a balloon by bonding wrapped layers of the polymeric material together to form a tubular member, and preferably provided with a nonporous second layer or liner, to form an inflatable balloon.

In a method of making an expandable medical device or component thereof which embodies features of the invention, a sheet of porous polymeric material is wrapped, typically on a mandrel, to form a tube having a seam formed by adjacent edges of the sheet, a longitudinal axis, a first longitudinal section with the seam at a first angle relative to the longitudinal axis of the tubular body, and a second longitudinal section with the seam at a second angle greater than the first angle relative to the longitudinal axis of the tubular body. The tube is heated, as for example in an oven, to fuse the longitudinal edges of the wrapped sheet together, to form a tubular body having a fused seam.

The wrap angle is dependent upon the inner diameter of the resulting tubular body (i.e., the outer diameter of the mandrel on which the sheet is wrapped), and the width of the sheet of porous polymeric material, and the amount of overlap (if any) between the longitudinally adjacent wrapped portions of the sheet. In a presently preferred embodiment, the width of the sheet of porous polymeric material is substantially uniform along the length of the sheet. The substantially uniform width of the sheet may vary within the tolerances used for forming the sheet, and thus the width may vary typically by about ±5% along the length of the sheet. In order to change the wrap angle at a transition between the sections having different wrap angles the sheet of porous polymeric material is typically stretched and/or the amount by which the edge of the wrapped sheet overlaps the edge of the longitudinally adjacent portion of wrapped material is changed as the sheet is wrapped around the mandrel. However, a variety of methods may be used to increase the wrap angle, such as for example using a sheet having a varying width (i.e., a greater width in the portion of the length of the sheet forming the second section of the tubular body), or by wrapping the sheet on a varying diameter mandrel. In one embodiment, the sheet is wrapped such that the adjacent edges abut one another at least along the first section (i.e., the section having the fused seam at the first angle). However, in alternative embodiments, the sheet is wrapped such that the adjacent edges of the wrapped sheet along the first section are in an overlapping configuration, although typically with a lesser amount of overlap than in the remaining sections with the fused seam at a higher angle.

The sheet of polymeric material is wrapped along the length of the mandrel, and is typically wrapped multiple times back over the underlying length or layer in the opposite direction, to form multiple layers of the porous material which typically fuse together during formation of the fused seam. Thus, the tubular body typically comprises multiple layers of the wrapped sheet, with adjacent layers of the wrapped sheet having the fused seam at the given angle of the longitudinal section but oriented in opposite directions.

In one embodiment, during formation of the porous polymeric tubular body, the sheet of porous polymeric material is wrapped so that the first angle of the wrapped seam along a first longitudinal section is about 60 to about 75 degrees, preferably about 60 to about 70 degrees, and the second angle along a second longitudinal section is greater than the first angle and is about 70 to about 89 degrees, preferably about 75 to about 85 degrees. The wrapped sheet is then heated to fuse the wrapped seam and form the porous polymeric tubular body. However, in the embodiment in which the device component is a balloon, the resulting porous polymeric tubular body is typically stretched and/or compacted, or otherwise further processed, so that the angle of the fused seam may be increased or decreased along at least a portion of the length of the tubular body. The wrap angle decreases, and typically by about 30 to about 90 percent, more specifically about 70 to about 80 percent, as a result the porous polymeric tube being longitudinally stretched after formation of the fused seam. For example, in one embodiment, the wrap angle along the first section (i.e., the first angle) is originally about 60 to about 70 degrees after formation of the fused seam, and thereafter is caused to decrease to about 15 to about 25 degrees as a result of the porous polymeric tube being longitudinally stretched. In one embodiment, the porous polymeric tube is longitudinally compacted, typically after being longitudinally stretched, causing the wrap angle to increase as a result of the longitudinal compaction. Although the absolute value of the wrap angle of the fused seam may change as a result of such subsequent processing following the wrapping and fusing which forms the fused seam, the wrap angle of the fused seam in the finished balloon will remain greater in the second section than in the first section. For example, in one embodiment, first angle of the fused seam of the finished balloon (after any stretching or compacting processing) is about 10% to about 80% of the second angle and preferably 10% to about 50% of the second angle. In one embodiment, the fused seam of the finished balloon has a first angle of about 15 to about 75 degrees and preferably about 15 degrees to about 35 degrees, and a second angle (greater than the first angle) of about 25 to about 89 degrees and preferably about 50 degrees to about 89 degrees.

The expandable medical device or component thereof is provided with variable resistance to expansion along the length thereof due to the varying wrap angle of the porous polymeric sheet. In the embodiment in which the porous polymeric sheet forms a layer of a catheter balloon having at least one layer, the strength of the bond between the balloon and the catheter shaft is increased. Moreover, the working length of the balloon and tapered sections inflate to more clearly delineated sections due to the varying wrap angle, with the well defined working length facilitating stent positioning in the embodiment in which the balloon catheter is used for stent delivery. These and other advantages of the invention will become more apparent from the following detailed description and accompanying exemplary figures.

DETAILED DESCRIPTION OF THE INVENTION

Figure 1A:
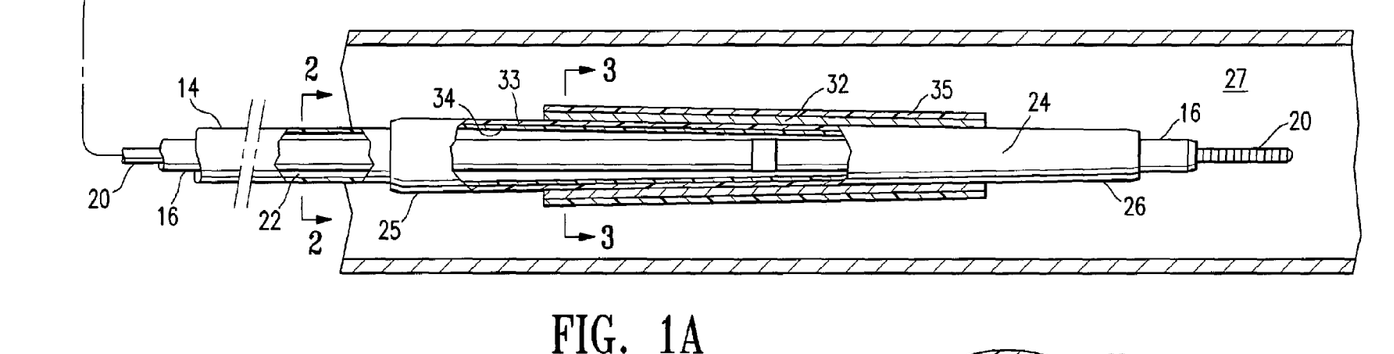
FIG. 1A is an elevational view, partially in section, of a stent delivery balloon catheter embodying features of the invention.
Figure 1B:
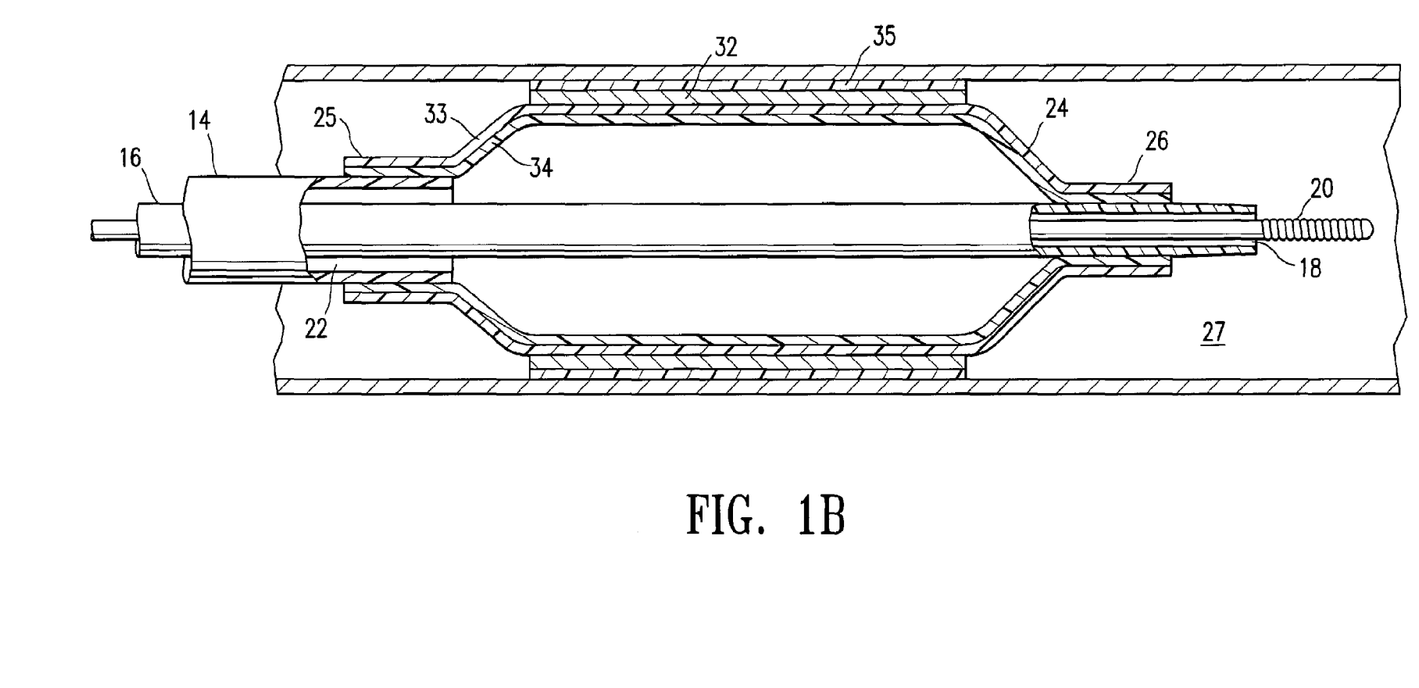
FIG. 1B illustrates the balloon of FIG. 1A fully inflated.
Figure 2:
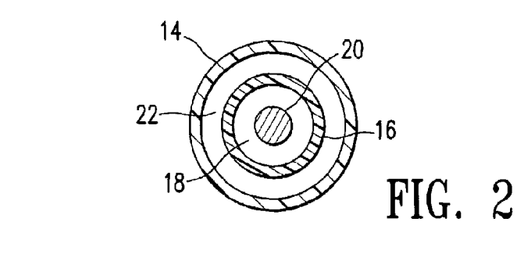
FIGS. 2 and 3 are transverse cross sectional views of the balloon catheter shown in FIG. 1, taken along lines 2—2, and 3—3, respectively.
Figure 3:
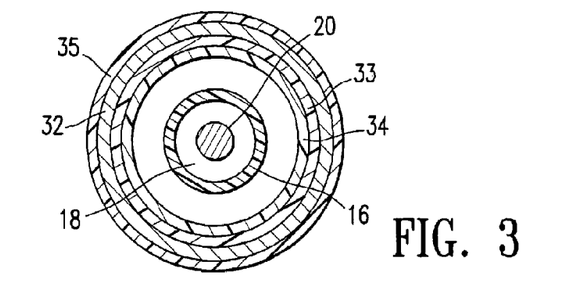

FIG. 1A illustrates an over-the-wire type stent delivery balloon catheter 10 embodying features of the invention. Catheter 10 generally comprises an elongated catheter shaft 12 having an outer tubular member 14 and an inner tubular member 16. Inner tubular member 16 defines a guidewire lumen 18 configured to slidingly receive a guidewire 20, and the coaxial relationship between outer tubular member 14 and inner tubular member 16 defines annular inflation lumen 22, as best shown in FIG. 2 illustrating a transverse cross section view of the distal end of the catheter shown in FIG. 1A, taken along line 2—2. An inflatable balloon 24 disposed on a distal section of catheter shaft 12 has a proximal skirt section 25 sealingly secured to the distal end of outer tubular member 14 and a distal skirt section 26 sealingly secured to the distal end of inner tubular member 16, so that its interior is in fluid communication with inflation lumen 22. An adapter 30 at the proximal end of catheter shaft 12 is configured to provide access to guidewire lumen 18, and to direct inflation fluid through arm 31 into inflation lumen 22. In the embodiment illustrated in FIG. 1A, the balloon 24 is shown prior to being fully inflated in a patient's body lumen 27, and with an expandable stent 32 having expandable tubular stent cover 35 mounted thereon. The distal end of the catheter may be advanced to a desired region of a patient's body lumen 27 in a conventional manner and balloon 24 may be inflated to expand covered stent 32, seating the covered stent 32 in the body lumen 27. FIG. 1B illustrates the balloon catheter 10 of FIG. 1A, with the balloon 24 fully inflated to expand the covered stent 32 within the body lumen 27. Inflated balloon 24 has a centrally located working length with stent 32 thereon, and proximal and distal inflatable sections (i.e., inflated tapered sections) at either end of the working length between the working length and the respective skirt section 25, 26 of the balloon.

In the embodiment illustrated in FIG. 1, balloon 24 has a first layer 33 and a second layer 34. In a presently preferred embodiment, the balloon 24 has at least one layer comprising a porous polymeric material, and preferably a microporous polymeric material having a node and fibril microstructure, such as ePTFE. In the embodiment illustrated in FIG. 1, first layer 33 is formed of ePTFE, and the second layer 34 is formed of a polymeric material preferably different from the polymeric material of the first layer 33. Although discussed below in terms of one embodiment in which the first layer 33 is formed of ePTFE, it should be understood that the first layer may comprise other materials including ultrahigh molecular weight polyethylene. The second layer 34 is preferably formed of an elastomeric material, including polyurethane elastomers, silicone rubbers, styrene-butadiene-styrene block copolymers, polyamide block copolymers, and the like. In a preferred embodiment, layer 34 forms an inner layer of balloon 24, although in other embodiments it may be on the exterior of the layer 33. Layer 34 limits or prevents leakage of inflation fluid through the microporous ePTFE layer 33 to allow for inflation of the balloon 24, and expands elastically to facilitate deflation of the balloon 24 to a low profile deflated configuration. The layer 34 may consist of a separate layer which neither fills the pores nor disturbs the node and fibril structure of the ePTFE layer 33, or it may at least partially fill the pores of the ePTFE layer 33.

The ePTFE layer 33 is formed according to a method which embodies features of the invention, in which a sheet of ePTFE is wrapped to form a tube, and then heated to fuse the wrapped material together. In accordance with a method of the invention, the sheet is wrapped such that the wrap angle varies along the length of the tube.

Figure 4:
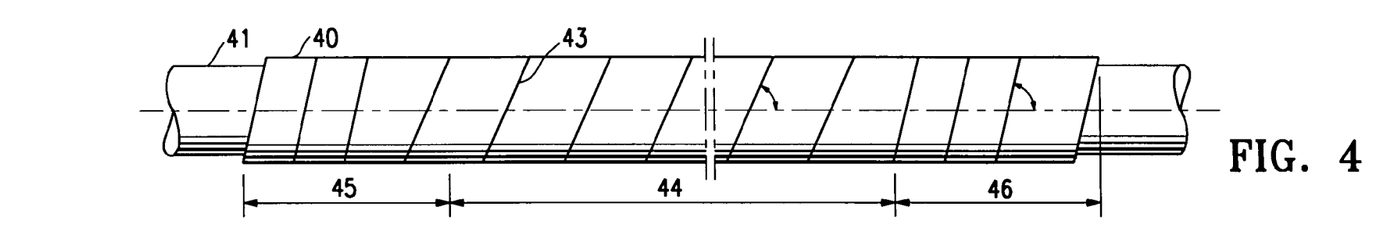
FIG. 4 is an elevational view of an assembly of a sheet of porous polymeric material wrapped on a mandrel to form a tube during formation of a layer of the balloon of FIG. 1, in which the sheet has a seam with a first angle at a central section of the tube and a second angle at end sections of the tube.
Figure 8:
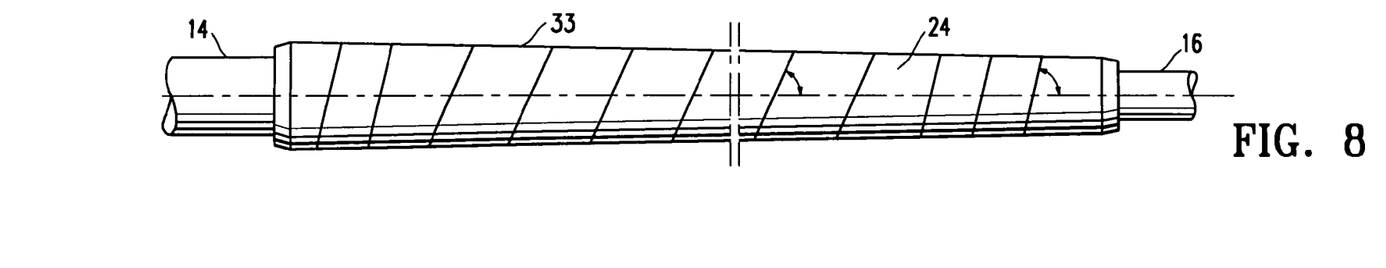
FIG. 8 illustrates the balloon formed from the tube of FIG. 4, with the balloon on the shaft inner and outer tubular members.

FIG. 4 illustrates an assembly of a sheet 40 of porous polymeric material (e.g., ePTFE) wrapped around a mandrel 41 and fused to form a porous polymeric tube, during the formation of the ePTFE layer 33 of the balloon 24 of FIG. 1. In the embodiment of FIG. 4, the tube has a centrally located section 44 with the fused seam 43 at a first angle of about 63 to about 65 degrees relative to the longitudinal axis of the tube, and a first end section 45 with the fused seam 43 at a second angle of about 76 to about 78 degrees, and a second end section 46 with the fused seam 43 a third angle about equal to the second angle. Although illustrated at about 76 degrees in FIG. 4, it should be understood that in a presently preferred embodiment the second angle is preferably as close to 90 degrees as possible while allowing the sheet 40 to progress helically along the length of the mandrel 41. FIG. 8 illustrates the balloon 24 having layer 33 formed from the tube of FIG. 4, with the balloon on the shaft inner and outer tubular members 14, 16.

Figure 5:
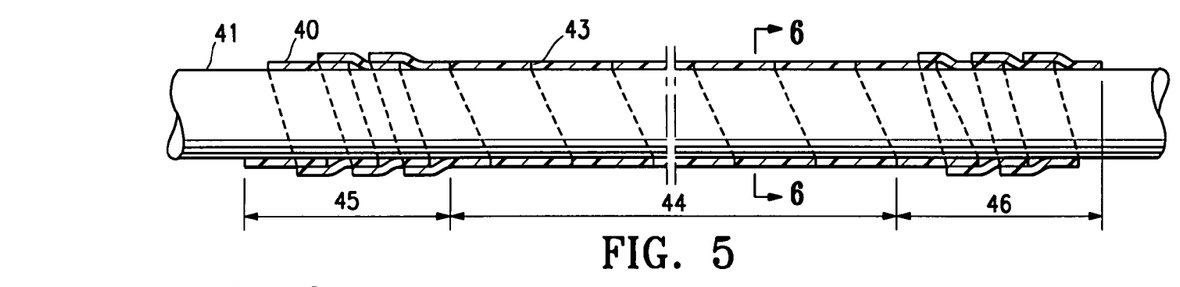
FIG. 5 illustrates the assembly shown in FIG. 4, partially in longitudinal cross section.
Figure 6:
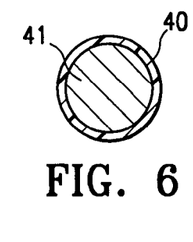
FIG. 6 is a transverse cross sectional view of the assembly shown in FIG. 5, taken along line 6—6.

Although the fused seam 43 is illustrated in FIG. 4 and FIG. 8 as highly visible lines along the tube for ease of illustration, it should be understood that the fused seam 43 in the finished balloon is generally not highly visible to the naked eye. FIG. 5 illustrates a longitudinal cross sectional view of the assembly of FIG. 4, and FIG. 6 illustrates a transverse cross sectional view of the assembly of FIG. 5, taken along lines 6—6.

Preferably the centrally located section 44 of the tube of FIG. 4 corresponds to the inflatable sections of the balloon 24 of FIG. 1 (i.e., the inflatable working length with the stent 32 mounted thereon, and the inflated proximal and distal tapered sections on either end of the working length). The first and second end sections 45, 46 correspond to the proximal and distal skirt sections 25, 26 of balloon 24 of FIG. 1, which are secured to the catheter shaft 12. The angles illustrated in FIG. 4 are the angles which are present following wrapping and fusing of the sheet prior to any further processing steps, such as longitudinally stretching and/or compacting the porous polymeric tube, which may change the wrap angles. Additionally, inflation of the balloon typically increases the first wrap angle of the central section of the balloon as the wrapped sheet unwinds during expansion.

The sheet 40 of polymeric material is preferably wrapped along a length of the mandrel 41 to form at least one layer of wrapped material. In a presently preferred embodiment, multiple layers of polymeric material are wrapped on the mandrel, by wrapping the sheet 40 down the length of the mandrel 41 to form a first layer and then back again over the first layer one or more times to form additional layers, which in one embodiment results in three to five layers, preferably about four layers of material forming the ePTFE layer 33 of balloon 24. Thus, although illustrated in FIG. 5 as a single layer of wrapped material, it should be understood that the sheet 40 typically forms multiple layers on the mandrel 41. The multiple layers of ePTFE are typically fused together to produce the tube forming layer 33 of balloon 24. Because the adjacent layers of the sheet are wrapped in opposite directions along the length of the mandrel, the adjacent layers have the fused seam oriented in opposite directions. However, the respective angles of the fused seam (i.e., first, second or third angles) of the various longitudinal sections of the tube remain the same in the adjacent layers, although in opposite directions.

In the embodiment of FIG. 1, the sheet 40 is a long strip of polymeric material having longitudinal edges along the length of the strip which are longer than the width of the sheet 40. The sheet 40 is wrapped on the mandrel 41 so that the longitudinal edges of the sheet 40 are brought together in an abutting or overlapping relation, and the fused seam 43 joins the abutting or overlapping edges together. In a presently preferred embodiment, the fused seam 43 is formed by edges of the wrapped sheet 40 which abut one another, at least along the centrally located section 44.

In order to transition from the first angle to the second/third angle during wrapping of the sheet 40 from one end to the other end of the mandrel 41, the sheet 40 is typically stretched and/or caused to overlap a portion of the preceding turn of the sheet 40 in a transition section. In the embodiment illustrated in FIG. 5, portions of the preceding turns of the sheets are covered by the adjacent turn of the sheet in the transition sections and in the first and second end sections 45, 46, in order to form the first and second angles. Although FIG. 5 illustrates an embodiment in which the edges of the sheet 40 overlap one another along the first and second end sections 45, 46, to form the seam having a larger angle than the seam along the central section 44, it should be understood that in alternative embodiments the edges of the sheet abut one another along the first and second end sections 45, 46, as for example by the sheet 40 being stretched (to change the width of the sheet) during winding of the first and second end sections 45, 46. In the embodiment of FIG. 5, the width of the sheet 40 and the outer diameter of the mandrel 41 are such that the sheet 40 can be wrapped with abutting edges forming the seam at an angle of about 65 degrees in the central section 44.

Figure 7:
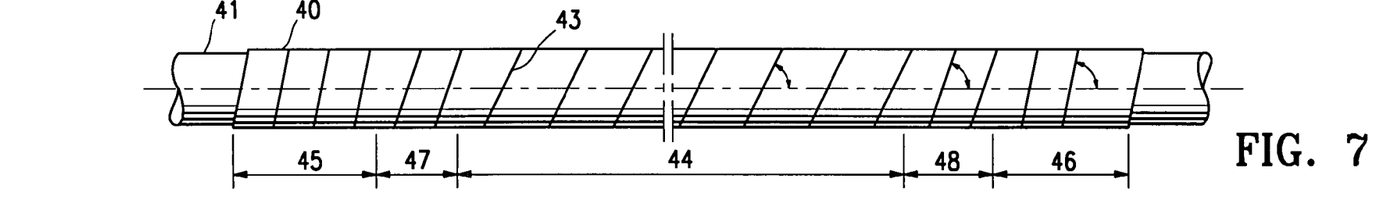
FIG. 7 is an elevational view of an assembly of a sheet of porous polymeric material wrapped on a mandrel during formation of a layer of the balloon of FIG. 1 in an alternative embodiment in which the sheet has a seam with an intermediate angle between the first angle of the central section and the second angle of the end sections.

In the embodiment of FIGS. 4 and 5, the fused seam angle transitions directly from the first to the second angle. However, in alternative embodiments, an intermediate longitudinal section is provided between the section with the fused seam at the first angle and the other sections of the tube, the intermediate section having an intermediate angle greater than the first angle and less than the second/third angles. The intermediate angle provides a section having greater resistance to expansion than the section with the fused seam at the first angle, and less resistance to expansion than the sections with the second/third angles. FIG. 7 illustrates an assembly of a wrapped sheet 40 of porous polymeric material on mandrel 41, with proximal and distal intermediate sections 47, 48 having the fused seam at an intermediate angle between the first and second/third angles. In the embodiment of FIG. 7, the intermediate angle is about 70 degrees, although a variety of suitable intermediate angles may be used. In one embodiment, the sheet 40 of porous polymeric material is wrapped so that the intermediate angle, prior to any stretching or compacting of the porous polymeric tube, is about 65 to about 85 degrees, more particularly about 68 to about 75 degrees. The intermediate angle in the finished balloon (after any stretching and/or compacting of the porous polymeric tube) is typically about 85% to about 95% of the second angle, and more specifically is typically about 20 to about 85 degrees. The intermediate sections 47, 48 correspond at least in part to the inflatable proximal and distal sections (i.e., inflated tapered sections) at either end of the working length of the balloon 24 in FIG. 1B. Although illustrated in FIG. 7 with the fused seam angle varying from about 78 degrees at the end sections 45, 46, to about 70 degrees at the intermediate sections 47, 48, and further to about 63 degrees at the central section 44, it should be understood that a tube with a variable fused seam angle in accordance with the invention may have a variety of sections with a variety of angles. The transitions between the intermediate sections 47, 48 and the adjacent longitudinal sections are formed as discussed above in relation to the embodiment of FIG. 5.

The sheet 40 is preferably a polymeric material having a microporous structure, which in one embodiment has a node and fibril structure, such as ePTFE. The sheet 40 preferably has the desired microstructure (e.g., porous and/or node and fibril) before being wrapped on the mandrel 41. In a presently preferred embodiment, the sheet 40 of ePTFE is partially-sintered before wrapping.

After the fused seam 43 is formed, the tubular body is typically further processed prior to being bonded to the layer 34 to form the balloon 24. Preferably, the tubular body is further processed by being stretched, sintered, compacted, and then sintered again, to provide the desired properties such as the desired dimension, and dimensional stability (e.g., to minimize changes in length occurring during inflation of the balloon). For example, in one embodiment, the tubular body is longitudinally stretched to thereby increase the length of the tubular body by about 50% to about 200%. After the longitudinal stretching, the tubular body is preferably compacted and heated to further sinter the material, to provide the desired performance characteristics for balloon 24. The tubular body is typically heated in an oven at about 360° C. to about 380° C., or to at least the melting point of the ePTFE. The stretching and/or compaction typically affects the angle of the fused seam. In one embodiment, the finished balloon layer 33 (prior to inflation of the balloon), produced from the tube of FIG. 7 having the fused seam at the angles shown in FIG. 7, has the fused seam at angles along at least some of the sections 44, 45, 46, 47, 48 which are less than the angles shown in FIG. 7 as a result of the further processing. The completed ePTFE layer 33 is then bonded to or otherwise combined with the elastomeric liner 34 to complete the balloon 24 with the balloon 24 secured to the catheter shaft 12.

The dimensions of catheter 10 are determined largely by the size of the balloon and guidewires to be employed, catheter type, and the size of the artery or other body lumen through which the catheter must pass or the size of the stent being delivered. Typically, the outer tubular member 14 has an outer diameter of about 0.025 to about 0.04 inches (0.064 to 0.10 cm), usually about 0.037 inches (0.094 cm), the wall thickness of the outer tubular member 14 can vary from about 0.002 to about 0.008 inches (0.0051 to 0.02 cm), typically about 0.003 to 0.005 inches (0.0076 to 0.013 cm).

The inner tubular member 16 typically has an inner diameter of about 0.01 to about 0.018 inches (0.025 to 0.046 cm), usually about 0.016 inches (0.04 cm), and wall thickness of 0.004 to 0.008 inches (0.01 to 0.02 cm). The overall length of the catheter 10 may range from about 100 to about 150 cm, and is typically about 143 cm. Balloon 24 typically has a length of about 5 to about 60 mm, and an inflated working diameter of about 2 to about 10 mm. In one embodiment, the skirt sections 25, 26 of the balloon 24 typically have a length of about 0.5 to about 7 mm, and the central working section of the balloon 24 has a length greater than the skirt sections and equal to about 5 to about 40 mm.

Inner tubular member 16 and outer tubular member 14 can be formed by conventional techniques, for example by extruding and necking materials already found useful in intravascular catheters such a polyethylene, polyvinyl chloride, polyesters, polyamides, polyimides, polyurethanes, and composite materials. The various components may be joined using conventional bonding methods such as by fusion bonding or use of adhesives. Although the shaft is illustrated as having an inner and outer tubular member, a variety of suitable shaft configurations may be used including a dual lumen shaft having a side-by-side lumens therein. Similarly, although the embodiment illustrated in FIG. 1 is an over-the-wire stent delivery catheter, balloons of this invention may also be used with other types of intravascular catheters, such as rapid exchange dilatation catheters. Rapid exchange catheters generally comprise a distal guidewire port in a distal end of the catheter, a proximal guidewire port in a distal shaft section distal of the proximal end of the shaft and typically spaced a substantial distance from the proximal end of the catheter, and a short guidewire lumen extending between the proximal and distal guidewire ports in the distal section of the catheter.

While the present invention is described herein in terms of certain preferred embodiments, those skilled in the art will recognize that various modifications and improvements may be made to the invention without departing from the scope thereof. Moreover, although individual features of one embodiment of the invention may be discussed herein or shown in the drawings of the one embodiment and not in other embodiments, it should be apparent that individual features of one embodiment may be combined with one or more features of another embodiment or features from a plurality of embodiments.

What is claimed is:

1. A balloon catheter, comprising:
   a) an elongated shaft having a proximal end, a distal end, and at least one lumen; and
   b) a balloon having at least a first layer comprising a tubular body formed of a wrapped sheet of porous polymeric material fused together with a fused seam at an angle relative to the longitudinal axis of the shaft which changes along a length of the tubular body, and having a proximal skirt section and distal skirt section sealingly secured to the shaft so that the balloon interior is in fluid communication with the at least one lumen of the shaft, the entire length of the skirt sections being sealingly secured to the shaft such that the balloon has an inflatable section extending from the proximal skirt section to the distal skirt section, with the angle of the fused seam along at least one of the proximal and the distal skirt sections being greater than the angle of the fused seam along the entire length of the inflatable section between the sealingly secured skirt sections.

2. The balloon catheter of claim 1 wherein the balloon has a second layer extending along the first layer and formed of a nonporous polymeric material.

3. The balloon catheter of claim 1 wherein at least a portion of an inflatable working portion of the balloon has the fused seam at a first angle, at least a portion of the distal skirt section has the fused seam at a second angle, and at least a portion of the proximal skirt section has the fused seam at a third angle relative to the longitudinal axis, the second and third angles being about equal, and greater than the first angle.

4. The balloon catheter of claim 1 wherein the balloon inflatable working portion is between a proximal and a distal inflatable portion, and at least a portion of the proximal and distal inflatable portions have the fused seam at an intermediate angle between the first angle and the second angle.

5. The balloon catheter of claim 4 wherein the intermediate angle is about 20 to about 85 degrees.

6. The balloon catheter of claim 4 wherein the first angle is about 20 to about 75 degrees.

7. The balloon catheter of claim 1 wherein the second and third angles are each about 25 to about 89 degrees.

8. The balloon catheter of claim 3 wherein the working portion of the balloon has a higher compliance at a given inflation pressure than inflatable portions of the balloon having the fused seam at a greater angle than the first angle.

9. The balloon catheter of claim 3 wherein the fused seam at the first angle along at least a portion of the balloon working portion comprises abutted edges of the wrapped sheet fused together.

10. The balloon catheter of claim 1 wherein the balloon is fused to the shaft, and has a burst pressure of about 250 to about 400 psi.

11. The balloon catheter of claim 8 wherein the tubular body comprises multiple layers of the wrapped sheet, and adjacent layers of the wrapped sheet have the fused seam oriented in opposite directions.

* * * * *

UNITED STATES PATENT AND TRADEMARK OFFICE
CERTIFICATE OF CORRECTION

| | |
|---|---|
| PATENT NO. | : 7,195,638 B1 |
| APPLICATION NO. | : 10/331858 |
| DATED | : March 27, 2007 |
| INVENTOR(S) | : Srinivasan Sridharan |

Page 1 of 1

It is certified that error appears in the above-identified patent and that said Letters Patent is hereby corrected as shown below:

Column 11,
Line 12, delete "claim 1" and insert instead -- claim 3 --

Column 12,
Line 1, delete "claim 1" and insert instead -- claim 3 --

Line 15, delete "claim 8" and insert instead -- claim 1 --

Signed and Sealed this

Twelfth Day of June, 2007

JON W. DUDAS
*Director of the United States Patent and Trademark Office*